(12) United States Patent
Hirose

(10) Patent No.: US 8,376,547 B2
(45) Date of Patent: Feb. 19, 2013

(54) ADAPTIVE OPTICAL APPARATUS AND IMAGING APPARATUS HAVING THE SAME

(75) Inventor: Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/907,849

(22) Filed: Oct. 19, 2010

(65) Prior Publication Data

US 2011/0102740 A1 May 5, 2011

(30) Foreign Application Priority Data

Oct. 30, 2009 (JP) ................. 2009-251422

(51) Int. Cl.
*A61B 3/14* (2006.01)
*A61B 3/10* (2006.01)
*A61B 3/00* (2006.01)

(52) U.S. Cl. ......... 351/206; 351/205; 351/221; 351/246

(58) Field of Classification Search ........... 351/200–246
See application file for complete search history.

(56) References Cited

U.S. PATENT DOCUMENTS

| 7,118,216 | B2 * | 10/2006 | Roorda | 351/205 |
| 7,275,824 | B2 * | 10/2007 | Hoshino | 351/206 |
| 7,367,672 | B2 * | 5/2008 | Akita | 351/206 |
| 7,407,285 | B2 * | 8/2008 | Lai et al. | 351/205 |
| 7,490,939 | B2 * | 2/2009 | Hirohara et al. | 351/205 |
| 7,537,340 | B2 * | 5/2009 | Yamaguchi et al. | 351/205 |

FOREIGN PATENT DOCUMENTS

JP    2007-14569 A    1/2007

* cited by examiner

*Primary Examiner* — Mohammed Hasan
(74) *Attorney, Agent, or Firm* — Canon U.S.A., Inc., IP Division

(57) ABSTRACT

An adaptive optical apparatus includes a wavelength separation unit configured to separate a beam emitted from a light source into a plurality of wavelength band beams, a plurality of light modulation units configured to modulate the respective plurality of wavelength band beams, a wavelength combining unit configured to combine the beams modulated by the plurality of light modulation units into a beam, and an illumination unit configured to illuminate a measured object with the beam output from the wavelength combining unit.

18 Claims, 8 Drawing Sheets

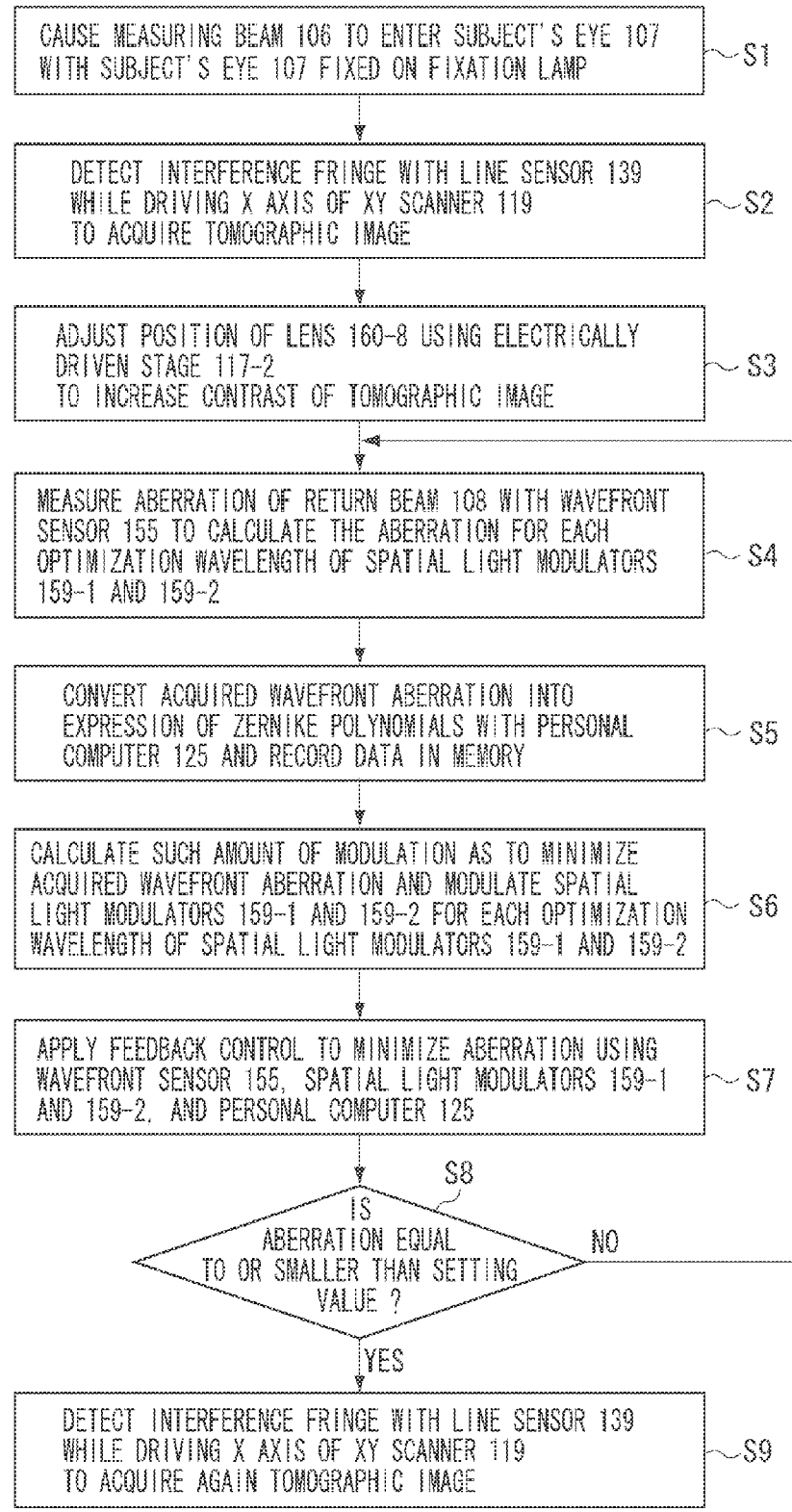

ADAPTIVE OPTICAL APPARATUS AND IMAGING APPARATUS HAVING THE SAME

BACKGROUND OF THE INVENTION

1. Field of the Invention

The present invention relates to an adaptive optical apparatus and an imaging apparatus having the adaptive optical apparatus.

2. Description of the Related Art

An optical coherence tomography (OCT) using multi-wavelength light wave interference is a method for acquiring a tomographic image of a sample, in particular, of a fundus, with a high resolution.

Hereinafter, an optical tomographic imaging apparatus for capturing an optical tomographic image with such an OCT is referred to as an OCT apparatus.

In recent years, the increased beam diameter of a measuring beam in a Fourier domain OCT apparatus has allowed acquiring the tomographic image of a retina with a high transverse resolution.

Along with the increase of the beam diameter of a measuring beam, the problem has arisen that the SN ratio and the resolution of a tomographic image are lowered due to aberration caused by the distortion of a curved surface and the ununiformity of a refractive index in a subject's eye when the tomographic image of a retina is acquired.

To solve the problem, an adaptive optical OCT apparatus with an adaptive optical system for measuring the aberration of a subject's eye with a wavefront sensor in real time to compensate for the aberration with a wavefront correction device has been developed to enable acquiring a tomographic image with a high transverse resolution.

Japanese Patent Application Laid-Open No. 2007-14569 discusses an ophthalmological photographing apparatus, as an apparatus using such an adaptive optical system, capable of acquiring a fundus image using an adaptive optical and a liquid crystal spatial phase modulator, a polygon mirror, and a galvanometer mirror in a scanning laser ophthalmoscope (SLO).

The ophthalmological photographing apparatus corrects the aberration caused in the subject's eye using the liquid crystal spatial phase modulator to avoid the deterioration of transverse resolution. A generally narrow-band semiconductor laser is used as a light source. Nothing has been written about the use of a wide-band light source in the OCT apparatus.

The above liquid crystal spatial phase modulator modulates a refractive index using the birefringence of a liquid crystal, so that the amount of modulation depends upon a wavelength. For this reason, if the OCT apparatus is formed using a wide-band light source, an improvement is required to acquire a high-resolution image.

If aberration is corrected using a phase wrapping technique, the influence becomes more prominent.

SUMMARY OF THE INVENTION

The present invention is directed to an optical imaging apparatus and an optical imaging method capable of reducing the influence of dependence of a spatial light modulation unit on a wavelength in an optical imaging apparatus having an adaptive optical system using a spatial phase modulation unit.

According to an aspect of the present invention, an adaptive optical apparatus includes a wavelength separation unit configured to separate a beam emitted from a light source into a plurality of wavelength band beams, a plurality of light modulation units configured to modulate the respective plurality of wavelength band beams, a wavelength combining unit configured to combine the beams modulated by the plurality of light modulation units into a beam, and an illumination unit configured to illuminate a measured object with the beam output from the wavelength combining unit.

An exemplary embodiment of the present invention can realize an optical imaging apparatus and an optical imaging method capable of reducing the influence of dependence of a spatial light modulation unit on a wavelength in an optical imaging apparatus having an adaptive optical system using a spatial phase modulation unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 7 illustrates a procedure for acquiring a tomographic image by the OCT apparatus according to the first exemplary embodiment of the present invention.

DESCRIPTION OF THE EMBODIMENTS

Various exemplary embodiments, features, and aspects of the invention will be described in detail below with reference to the drawings.

In the exemplary embodiment of the present invention, the OCT apparatus for capturing a subject's eye with a subject as an eye is described as an optical imaging apparatus. The OCT apparatus is applicable to other apparatus such as a scanning laser ophthalmoscope (SLO) as long as the other apparatus are an imaging apparatus for capturing an image using light.

In a first exemplary embodiment of the present invention, an OCT apparatus having an adaptive optical system with a high transverse resolution for capturing a tomographic image (OCT image) of a subject's eye in particular is described.

In the present exemplary embodiment, a Fourier domain OCT apparatus is formed in which the aberration of the subject's eye is corrected using a reflective spatial light modulator to acquire a tomographic image, allowing providing a good tomographic image irrespective of the diopter and aberration of the subject's eye.

The present exemplary embodiment is characterized in that a measuring beam is split into two beams based on wavelength, caused to enter two reflective spatial light modulators and modulated separately. The spatial light modulator is a reflective liquid-crystal spatial phase modulator using the orientation of liquid crystal. The spatial light modulator can have only to modulate the phase of light, and materials other than liquid crystals may be used.

The general configuration of the OCT apparatus according to the present exemplary embodiment is described below with reference to FIG. 1. An OCT apparatus 100 according to the present exemplary embodiment forms Michelson interferometer system as a whole as illustrated in FIG. 1.

Figure 1:
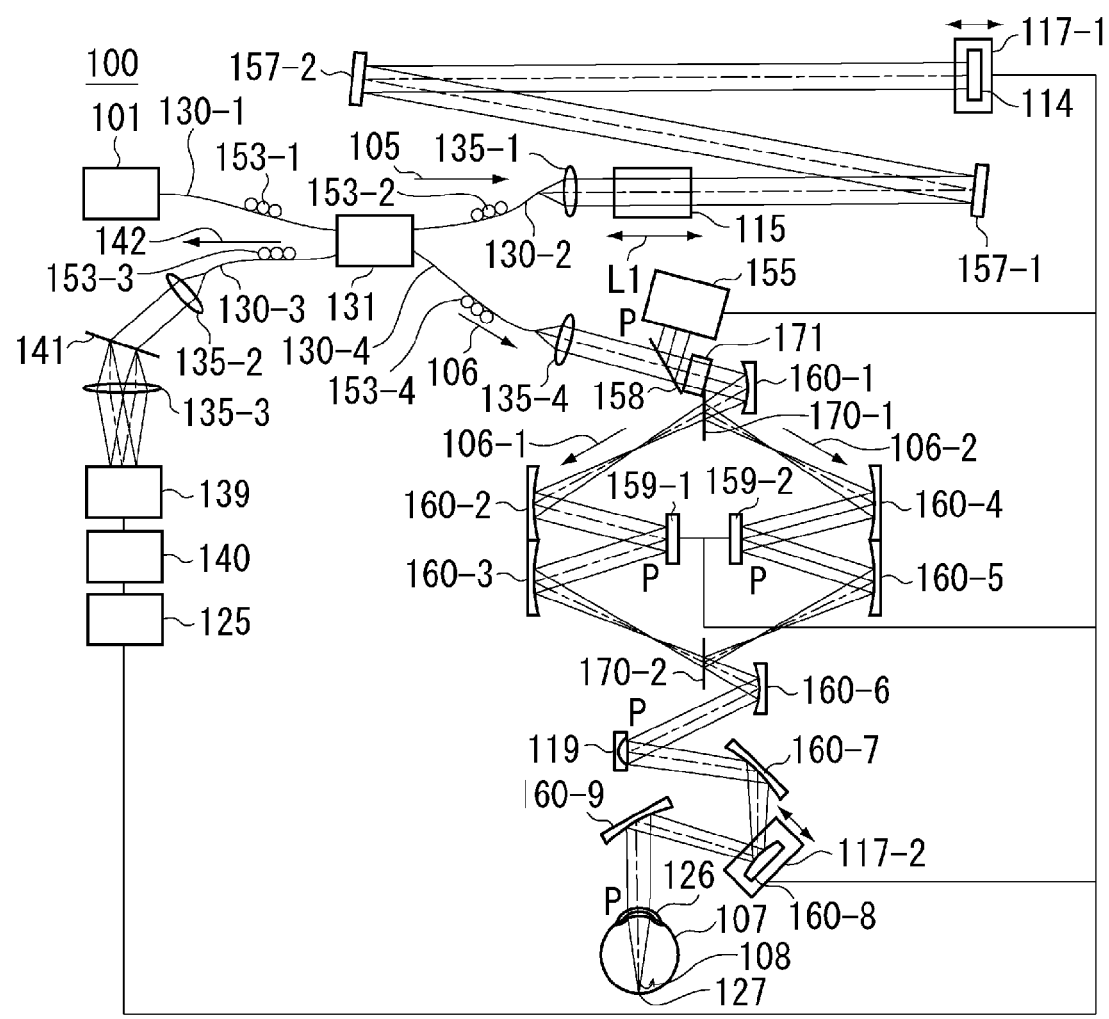
FIG. 1 is a schematic diagram illustrating the general configuration of an OCT apparatus according to a first exemplary embodiment of the present invention.

In FIG. 1, light emitted from a light source 101 is divided into a reference beam 105 and a measuring beam 106 at a ratio of 90:10 via an optical fiber 130-1 and an optical coupler 131. The measuring beam 106 is led to a subject's eye 107 being an object to be observed via a single mode fiber 130-4, dichroic mirrors 170-1 and 170-2, spatial light modulators 159-1 and 159-2, an XY scanner 119, spherical mirrors 160-1 to 160-9.

The measuring beam 106 is split into two beams for each wavelength by a first dichroic mirror 170-1. Then, the two beams are caused to enter the spatial light modulators 159-1 and 159-2 and combined into one beam by a second dichroic mirror 170-2.

The measuring beam 106 is reflected or scattered by the subject's eye 107 being an object to be observed and returned as a return beam 108. The return beam 108 is combined with the reference beam 105 by the optical coupler 131. Polarizing controllers 153-1 to 153-4 adjust the state of polarization between the measuring beam 106 and the reference beam 105.

After the reference beam 105 is combined with the return beam 108, the combined light is dispersed by a transmissive grating 141 for each wavelength and the dispersed light is caused to enter a line sensor 139.

The line sensor 139 converts light intensity into voltage for each position (wavelength). A signal of the voltage is used to form a tomographic image of the subject's eye 107.

The aberration of the return beam 108 (aberration measuring beam) is measured with a wavefront sensor (aberration measuring unit) 155.

The present exemplary embodiment is provided with a function that the spatial light modulators 159-1 and 159-2 are controlled to reduce the aberration, so that a good tomographic image can be acquired irrespective of the diopter and the aberration of the subject's eye 107.

In the present exemplary embodiment, although the entire optical system is formed of a reflective optical system mainly using spherical mirrors, the optical system may be formed of a refractive optical system using lenses instead of the spherical mirrors.

In the present exemplary embodiment, although a reflective spatial light modulator is used, a transmissive spatial light modulator may be used.

The periphery of the light source 101 is described below. The light source 101 uses a super luminescent diode (SLD) being a typical low-coherent light source. The central wavelength and the bandwidth thereof are 850 nm and 80 nm, respectively.

The bandwidth is an important parameter affecting the resolution in the optical axis direction of the acquired tomographic image. An ultrawide-waveband SLD is selected to acquire a tomographic image with a high longitudinal resolution.

Although, the SLD is selected as the type of a light source. However, a light source can have only to emit low-coherent light, and an amplified spontaneous emission (ASE) light source may be used.

Near-infrared light is suitable as a wavelength from the viewpoint of measurement of eyes. The wavelength affects the transverse resolution of the acquired tomographic image, so that a wavelength is desirably as short as possible and taken as 850 nm.

Other wavelengths may be selected depending on the measuring region of an object to be observed.

The optical path of the reference beam 105 is described below.

The reference beam 105 divided by the optical coupler 131 is led to a lens 135-1 via a single mode fiber 130-2 and adjusted so as to be parallel light with a beam diameter of 3 mm. The reference beam 105 is led to a mirror 114 being a reference mirror by mirrors 157-1 and 157-2. The optical path length of the reference beam 105 is adjusted to be substantially the same as that of the measuring beam 106 to allow the reference beam 105 and the measuring beam 106 to interfere with each other.

The reference beam 105 is reflected by the mirror 114 and led again to the optical coupler 131. A dispersion compensating glass 115, through which the reference beam 105 passes, compensates for dispersion at the time of the measuring beam 106 going to and returning from the subject's eye 107 for the reference beam 105.

The length of the dispersion compensating glass 115 is taken to be L1. The length L1 is taken to be 23 mm as a typical value of diameter of a Japanese average eyeball.

An electrically driven stage 117-1 is movable in the directions indicated by an arrow to allow the optical path length of the reference beam 105 to be adjusted and controlled.

The electrically driven stage 117-1 is driven under the control of a personal computer 125.

The optical path of the measuring beam 106 being the characteristic configuration of the present exemplary embodiment is described below.

The measuring beam 106 split by the optical coupler 131 is led to a lens 135-4 via a single mode fiber 130-4 and adjusted so as to be parallel light with a beam diameter of 3 mm.

The measuring beam 106 passes through a beam splitter 158 and a Glan-Thompson prism 171, reflected by the spherical mirror 160-1 and caused to enter a first dichroic mirror (a first splitting unit) 170-1. The measuring beam 106 is rendered to be linear polarized light parallel to the paper surface by the Glan-Thompson prism 171. Although polarization is adjusted by the Glan-Thompson prism 171, other optical elements such as a Glan-Taylor prism and a Savart plate may be used as long as they can render the measuring beam to linear polarized light.

The measuring beam 106 is split into a first measuring beam 106-1 formed mainly of components with a wavelength of 850 nm or longer and led to a first optical path and a second measuring beam 106-2 formed mainly of components with a wavelength of 850 nm or shorter and led to a second optical path.

The dichroic mirrors 170-1 and 170-2 transmit components with a wavelength of approximately 850 nm or longer and reflects components with a wavelength not longer than 850 nm.

The first measuring beam 106-1 on the first optical path is modulated by a first spatial light modulator 159-1 via the spherical mirror 160-2 and caused to enter a second dichroic mirror (a second splitting unit) 170-2 positioned on the side of a subject via the spherical mirror 160-3.

The first spatial light modulator 159-1 is optimized for a wavelength of 870 nm to have a function to modulate light with a wavelength of 850 nm to 890 nm.

The second measuring beam 106-2 on the second optical path is modulated by a second spatial light modulator 159-2 via the spherical mirror 160-4 and caused to enter a second dichroic mirror 170-2 via the spherical mirror 160-5.

The second spatial light modulator 159-2 is optimized for a wavelength of 830 nm to have a function to modulate light with a wavelength of 810 nm to 850 nm.

The spatial light modulators 159-1 and 159-2 are arranged in the direction in which the phase of P polarization (parallel to the paper surface) is modulated.

The first measuring beam 106-1 is combined with the second measuring beam 106-2 by the second dichroic mirror 170-2. The combined light is caused to enter the mirror of the XY scanner 119 via a mirror 160-6.

For the sake of simplicity, the XY scanner 119 is illustrated as a single mirror. Actually, however, an X scanning mirror and a Y scanning mirror are adjacently arranged and perform a raster scanning over a retina 127 in the direction perpendicular to the optical axis. The center of the measuring beam 106 is adjusted to agree with the rotation center of the mirror of the XY scanner 119. The spherical mirrors 160-7 to 160-9 are optical systems for scanning over the retina 127 and have a function to scan the measuring beam 106 over the retina 127 with the vicinity of the cornea 126 set as a fulcrum.

The beam diameter of the measuring beam 106 entering the retina 127 is 4 mm, but may be further increased to acquire a tomographic image higher in transverse resolution.

An electrically driven stage 117-2 is movable in the directions indicated by an arrow to allow the position of the spherical mirror 160-8 being an attached spherical mirror to be adjusted and controlled by the personal computer 125.

Adjusting the position of the spherical mirror 160-8 focuses the measuring beam 106 on a predetermined layer of the retina 127 of the subject's eye 107 to allow observation.

The above configuration is adaptable for a case where the subject's eye 107 is abnormal in refraction.

The measuring beam 106 enters the subject's eye 107 to turn into the return beam 108 by reflection and scattering from the retina 127, is led again by the optical coupler 131, and reaches the line sensor 139.

The return beam 108 is split into light beams for each wavelength (850 nm or more or not more than 850 nm), and the light beams are then modulated by the spatial light modulators 159-1 and 159-2 and combined by the first dichroic mirror 170-1.

Part of the return beam 108 split by the beam splitter 158 is caused to enter the wavefront sensor 155 to measure the aberration of the return beam 108. The wavefront sensor 155 is electrically connected to the personal computer 125.

The spherical mirrors 160-1 to 160-9 are arranged so that the cornea 126, the XY scanner 119, the wavefront sensor 155, and the spatial light modulators 159-1 and 159-2 are made optically conjugate with one another. The positions where they are conjugate with one another are indicated by letter "P." For this reason, the wavefront sensor 155 can measure the aberration of the subject's eye 107. Furthermore, the spatial light modulators 159-1 and 159-2 can correct the aberration of the subject's eye 107. Still furthermore, the spatial light modulators 159-1 and 159-2 are controlled in real time based on the acquired aberration to allow correcting the aberration caused in the subject's eye 107 and acquiring a tomographic image higher in transverse resolution.

An aspheric surface mirror or a freeform surface mirror may be used instead of the spherical mirrors 160-1 to 160-9.

Although the measuring beam 106 is split for each wavelength using the dichroic mirrors 170-1 and 170-2, other elements can be used as long as the elements can split the measuring beam 106 for each wavelength. For example, a dichroic prism may be used.

The spherical mirror 160-8 may be replaced with a cylindrical mirror depending on the aberration of the subject's eye 107 (refractive error).

A new lens can be added to the optical path of the measuring beam 106.

Although aberration is measured using the measuring beam 106 and the wavefront sensor 155, another light source can be used to measure the aberration. Furthermore, another optical path may be formed to measure the aberration. Light for measuring the aberration can be caused to enter using a beam splitter between the spherical mirror 160-9 and the cornea 126, for example.

Although the single wavefront sensor 155 is used to calculate the amount of modulation of the two spatial light modulators 159-1 and 159-2 optimized for wavelengths different from each other, conjugate points may be provided on the two optical paths divided for each wavelength to arrange wavefront sensors on the points and measure the aberration for each wavelength.

At the back of the spherical mirror 160-1, the measuring beam 106 is split into the first measuring beam 106-1 and the second measuring beam 106-2 using the dichroic mirror 170-1. However, the measuring beam 106 may be split at another place to form a measuring optical path.

Figure 2:
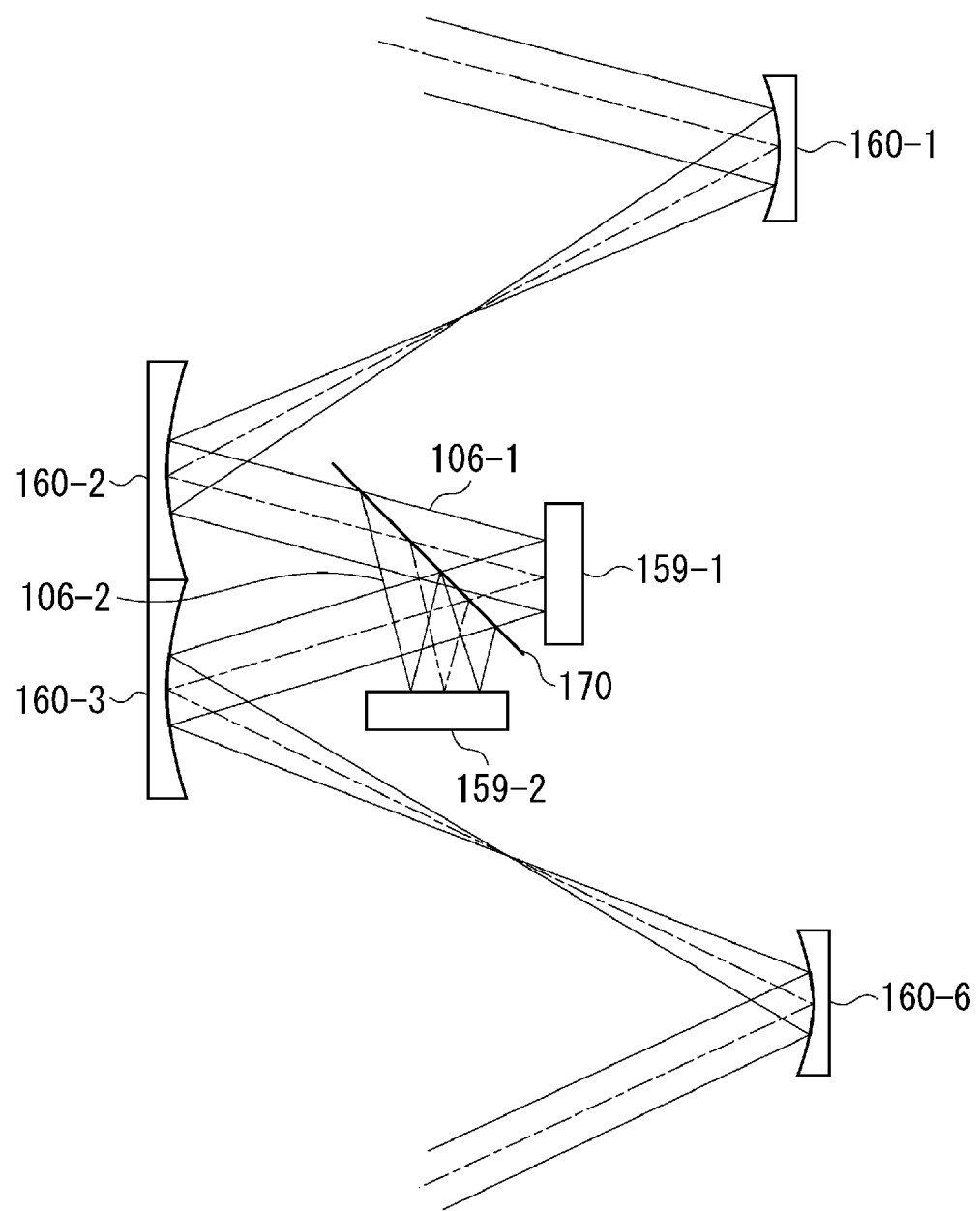
FIG. 2 is a schematic diagram illustrating the general configuration of the OCT apparatus according to the first exemplary embodiment of the present invention.

As illustrated in FIG. 2, for example, at the back of the spherical mirror 160-2, the measuring beam 106 may be split into the first measuring beam 106-1 and the second measuring beam 106-2 using the dichroic mirror 170. The first measuring beam 106-1 is modulated by the first spatial light modulator 159-1, passes through the dichroic mirror 170, and enters the spherical mirror 160-3.

Similarly, the second measuring beam 106-2 is modulated by the second spatial light modulator 159-2, is reflected by the dichroic mirror 170, and enters the spherical mirror 160-3.

Thereby, the dichroic mirror 170 can be used as the above two dichroic mirrors 170-1 and 170-2. Although a reflective liquid crystal spatial phase modulator is used as the spatial light modulators 159-1 and 159-2, a transmissive liquid crystal spatial phase modulator may be used.

Figure 3:
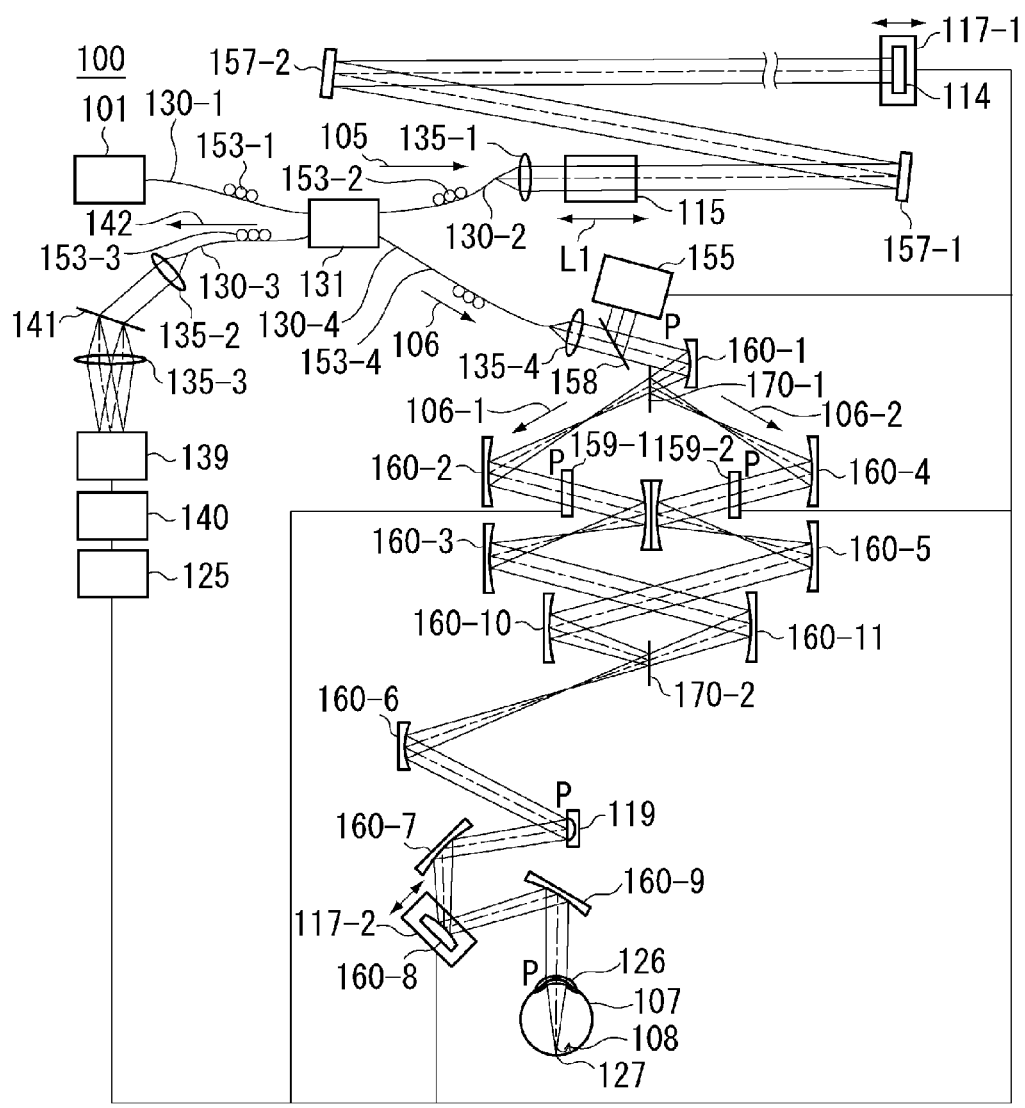
FIG. 3 is a schematic diagram illustrating the general configuration of the OCT apparatus according to the first exemplary embodiment of the present invention.

As illustrated in FIG. 3, for example, the spatial light modulator 159 may be replaced with the transmissive liquid crystal spatial phase modulator. The configuration in FIG. 3 is similar to that in FIG. 2 excepting for the type of the spatial light modulator 159 and the addition of the spherical mirrors 160-10 and 160-11, so that the similar components are given the same reference numerals or characters to avoid the description thereof.

The measuring system of the OCT apparatus according to the present exemplary embodiment is described below.

The OCT apparatus 100 can provide a tomographic image (OCT image) formed by the intensity of an interference signal by a Michelson interferometer.

The measuring system thereof is formed such that the return beam 108 being light reflected or scattered by the retina 127 is combined with the reference beam 105 by the optical coupler 131.

The combined light 142 is caused to enter the transmissive grating 141 via an optical fiber 130-3 and a lens 135-2.

The combined light 142 is dispersed for each wavelength by the transmissive grating 141 and concentrated by the lens 135-3. The intensity of the light is converted into voltage for each position (wavelength) by the line sensor 139.

Specifically, an interference fringe of a spectrum region on a wavelength axis is observed on the line sensor 139.

A voltage signal group acquired by the line sensor 139 is converted into a digital value by a frame grabber 140. Data processing is performed by the personal computer 125 to form a tomographic image.

The line sensor 139 has 1024 pixels and provides the intensity of the combined light 142 for each wavelength (1024 divisions).

Part of the return beam 108 split by the beam splitter 158 is caused to enter the wavefront sensor 155 to measure the aberration of the return beam 108.

The wavefront sensor 155 is a Shack-Hartmann wavefront sensor.

The acquired aberration is represented using Zernike polynomials, which indicates the aberration of the subject's eye 107.

The Zernike polynomials are made up of terms of tilt, defocus, astigmatism, coma, and trefoil.

A method for acquiring a tomographic image using the OCT apparatus is described below.

The OCT apparatus 100 can acquire the tomographic image of the retina 127 by controlling the XY scanner 119 to acquire an interference fringe by the line sensor 139 (refer to FIG. 1). A method for acquiring a tomographic image (a plane parallel to an optical axis) of the retina 127 is described with reference to FIGS. 4A to 4C.

Figure 4A:
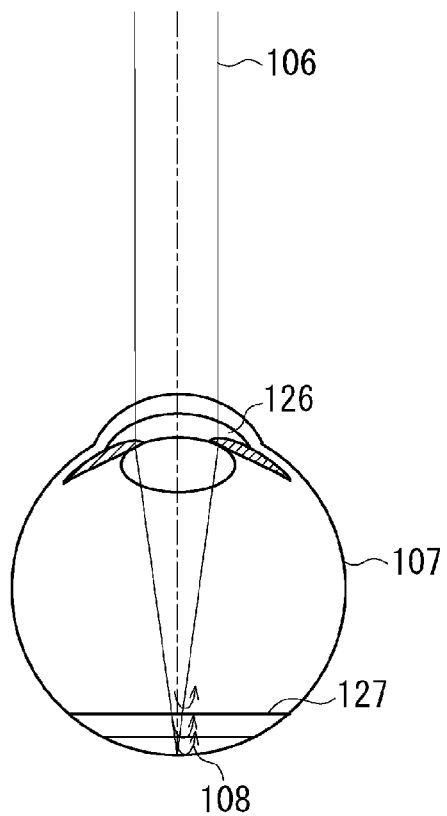
FIGS. 4A to 4C illustrate a method for acquiring a tomographic image by the OCT apparatus according to the first exemplary embodiment of the present invention.

FIG. 4A is a schematic diagram of the subject's eye 107 and illustrates that the subject's eye 107 is observed with the OCT apparatus 100.

As illustrated in FIG. 4A, the measuring beam 106 is caused to enter the retina 127 via the cornea 126 to turn into the return beam 108 by reflection and scattering in various positions. The return beam 108 is accompanied with time lag in respective positions and reaches the line sensor 139.

An interference fringe can be detected by the line sensor 139 only if the optical path length of the reference optical path is substantially equal to that of the measuring optical path because the bandwidth of the light source 101 is wide and the coherence length thereof is short.

As describe above, the interference fringe acquired by the line sensor 139 is the one in a spectrum region on the wavelength axis.

The interference fringe being information on the wavelength axis is converted into an interference fringe on an optical frequency axis in consideration of the characteristics of the line sensor 139 and the transmissive grating 141.

Furthermore, the converted interference fringe on the optical frequency axis is subjected to an inverse Fourier transform to produce luminance information in the depth direction.

Figure 4B:
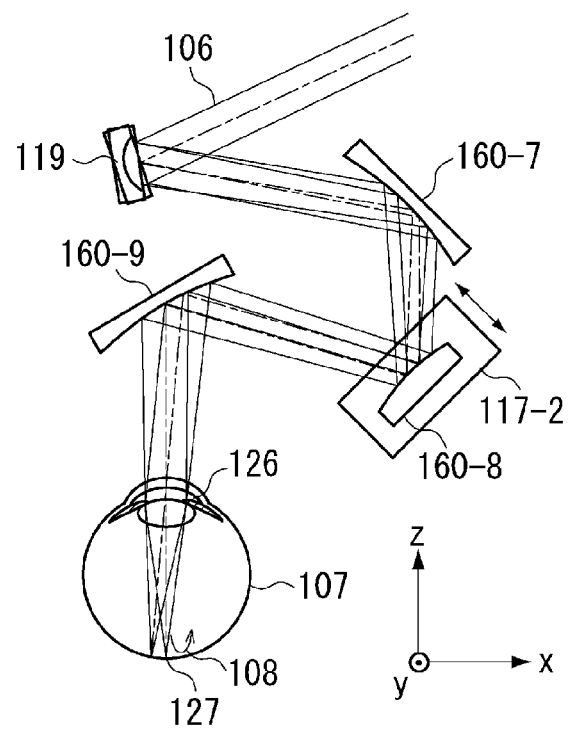

As illustrated in FIG. 4B, the interference fringe is detected while the X axis of the XY scanner 119 is being driven to allow acquiring interference fringes for each position of each X axis, more specifically, to allow acquiring luminance information in the depth direction for each position of each X axis.

Figure 4C:
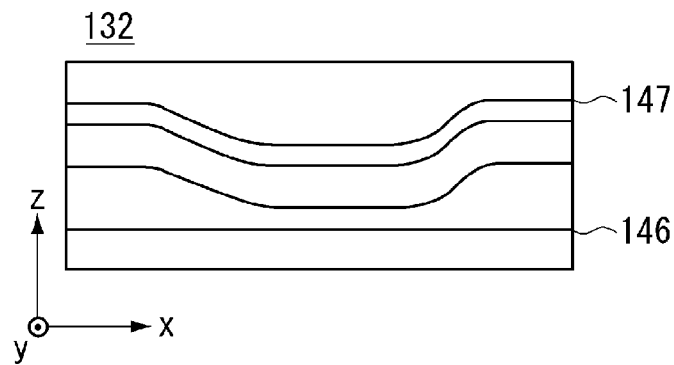

As a result, the two dimensional distribution of intensity of the return beam 108 on the XZ plane, i.e., a tomographic image 132, is acquired (refer to FIG. 4C).

As described above, the tomographic image 132 is originally an image in which the intensity of the return beam 108 is arranged in an array form. For example, the tomographic image 132 is displayed with the intensity applied to a gray scale. Only the boundary of the acquired tomographic image is emphatically displayed here. A retinal pigmented epithelium 146 and an optic nerve fiber layer 147 are illustrated in FIG. 4C.

The configuration of the spatial light modulator being the characteristic configuration of the present exemplary embodiment is described below with reference to FIGS. 5A and 5B.

There is considered a case where the measuring beam 106 is imaged on the retina 127 if the subject's eye 107 has a refractive error of spherical degree of −3D (myopia) and an entrance pupil diameter is 4 mm.

The modulation surface of an LCOS spatial light modulator (X10468-02), produced by Hamamatsu Photonics K.K., being the above spatial light modulator 159 is 12 mm in diameter. A pixel size is 20 μm in diameter. The number of pixels to be used is 600×600.

Figure 5A:
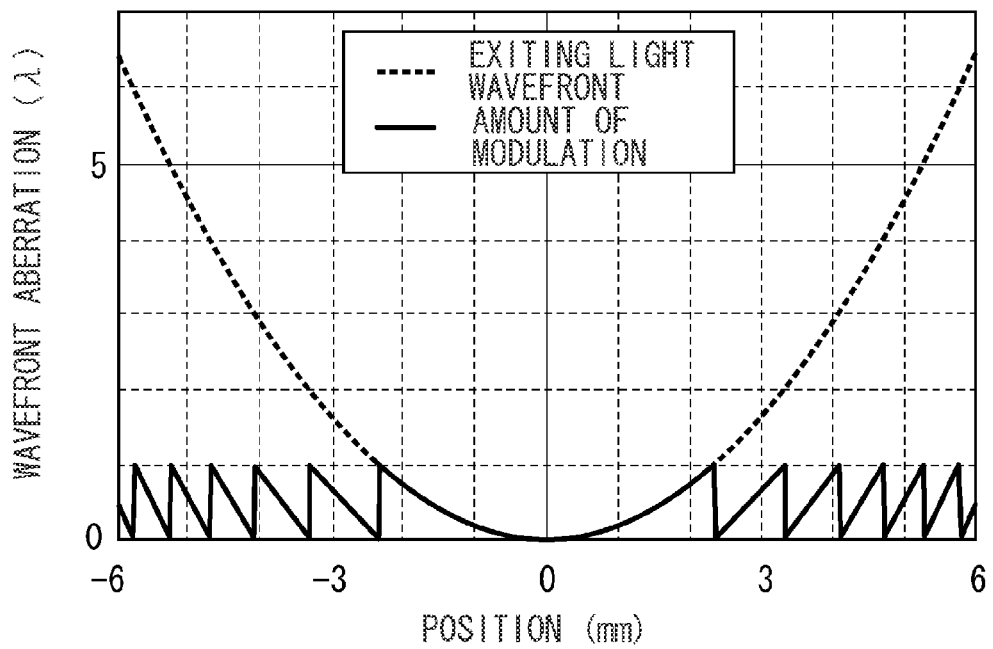
FIGS. 5A and 5B illustrate the wavefront aberration in the OCT apparatus according to the first exemplary embodiment of the present invention.

The wavefront of the measuring beam 106 exiting from the modulation surface of the spatial light modulators 159-1 and 159-2 to correct the refractive error is indicated by a broken line in FIG. 5A.

The maximum amount of modulation of the spatial light modulator 159 is λ. The wavefront indicated by the broken line cannot be directly produced, so that the wavefront is produced using a phase wrapping technique.

When the phase wrapping technique is used, the amount of modulation for realizing the wavefront indicated by the broken line is indicated by a solid line. The abscissa indicates coordinates on the modulation surface and the ordinate (direction+indicates delay in phase) indicates wavefront.

Figure 5B:
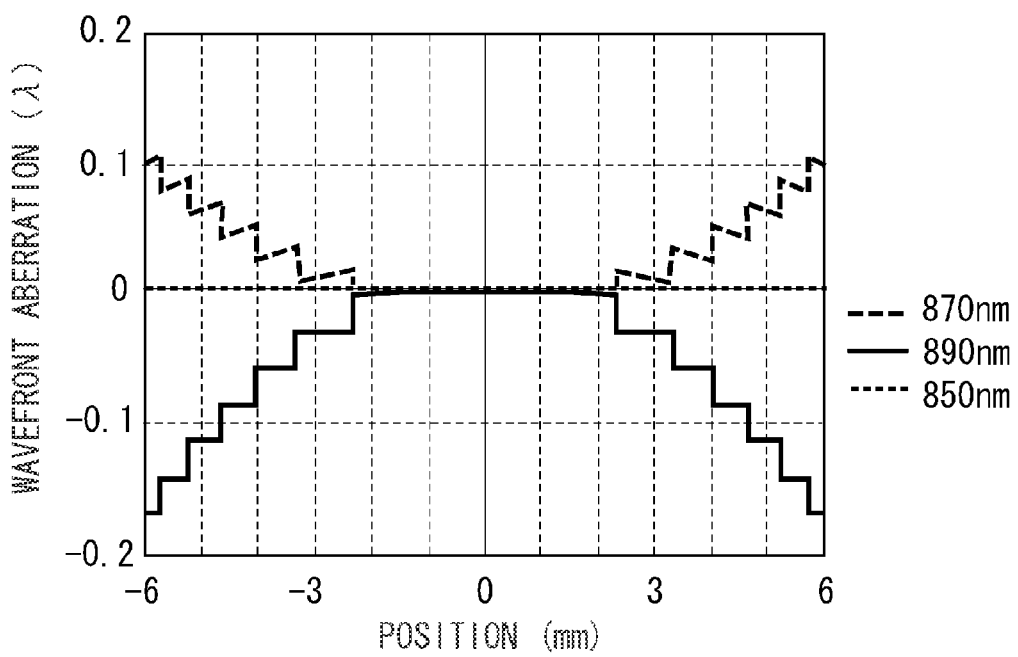

A residue ("a desired amount of modulation"−"an actual amount of modulation") estimated in the case where the amount of modulation illustrated in FIG. 5A is realized by the spatial light modulator 159-1 is indicated for each wavelength in FIG. 5B.

The abscissa indicates position coordinates (mm) on the spatial light modulator and the ordinate indicates wavefront aberration (λ). As described above, the spatial light modulator 159-1 is optimized for a wavelength of 870 nm to have a function to modulate light with a wavelength of 850 nm to 890 nm.

Figure 6A:
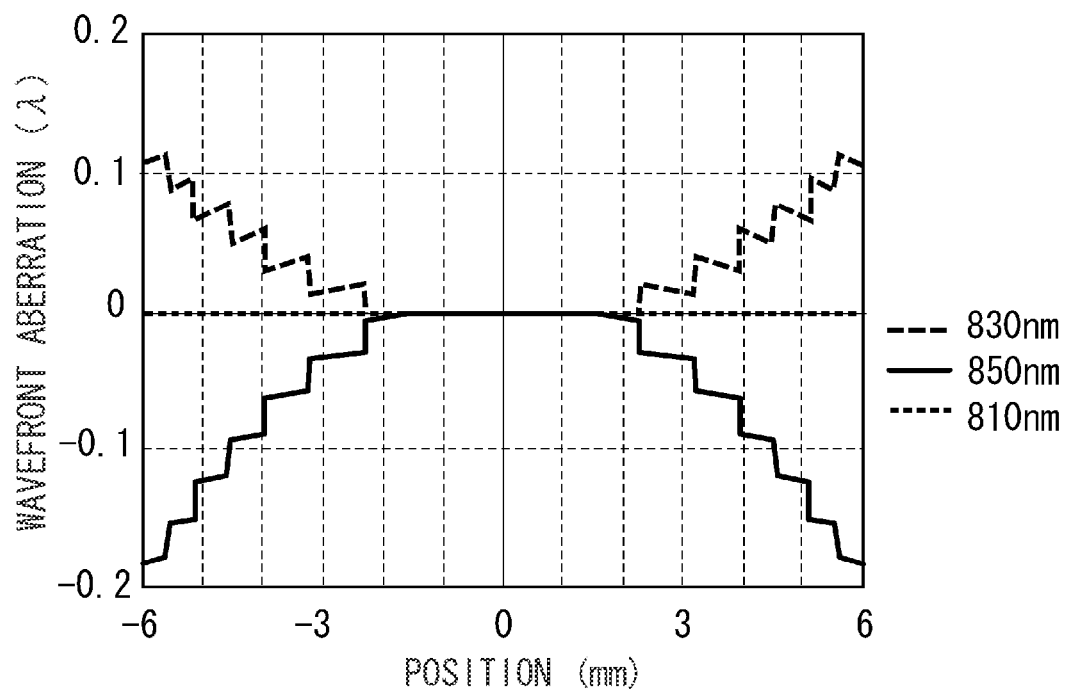
FIGS. 6A and 6B illustrate the wavefront aberration in the OCT apparatus according to the first exemplary embodiment of the present invention.

Similarly, a residue estimated in the case where the amount of modulation illustrated in FIG. 5A is realized by the spatial light modulator 159-2 is indicated for each wavelength in FIG. 6A.

As described above, the spatial light modulator 159-2 is optimized for a wavelength of 830 nm to have a function to modulate light with a wavelength of 810 nm to 850 nm.

Figure 6B:
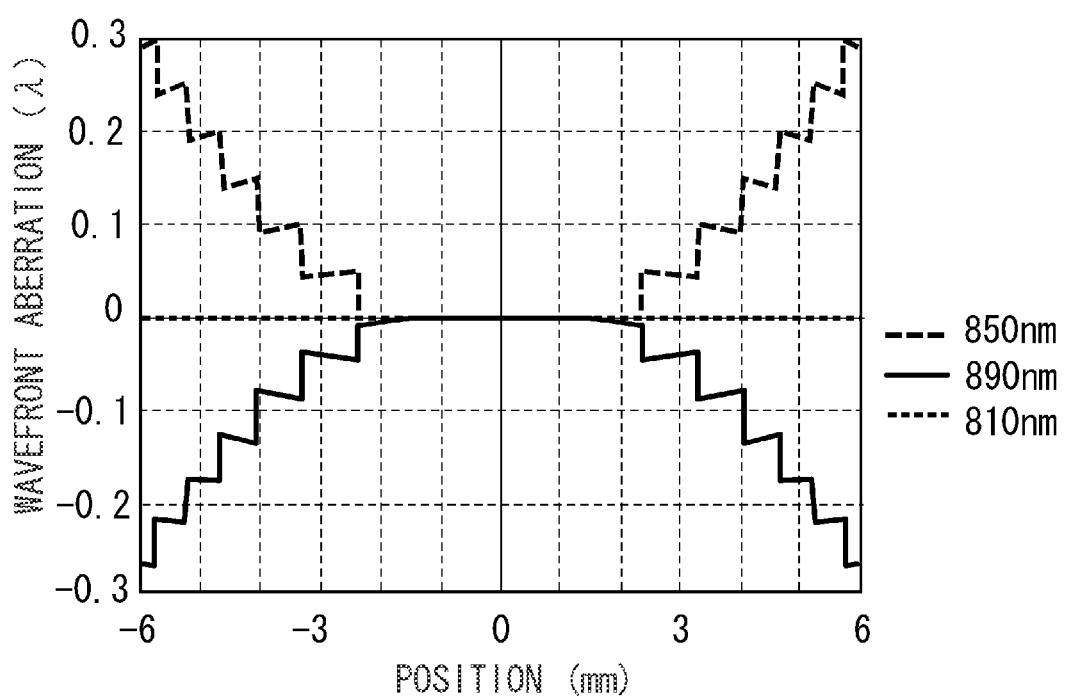

For the sake of reference, a residue estimated in the case where the amount of modulation illustrated in FIG. 5B is modulated by one spatial light modulator with respect to light with a wavelength of 810 nm to 890 nm is indicated in FIG. 6B. The spatial light modulator is optimized for a wavelength of 850 nm.

When FIGS. 5B, 6A, and 6B are compared with one another, the residue in the present exemplary embodiment is suppressed to as small as about 0.3λ (PV) to allow improvement of the tomographic image resolution and contrast.

The procedure for acquiring a tomographic image using the OCT apparatus is described below with reference to FIGS. 1 to 7. FIG. 7 is a flow chart illustrating the procedure for acquiring a tomographic image in the OCT apparatus 100. More specifically, FIG. 7 illustrates the procedure for acquiring a tomographic image of the retina 127 with a high transverse resolution by correcting the aberration of the myopic and astigmatic subject's eye 107 using the spatial light modulators 159-1 and 159-2.

Needless to say, even if the subject's eye 107 is merely myopic or hyperopic, the similar procedure can be used.

The tomographic image is acquired continuously, for example, in the following steps (1) to (9). Alternatively, the tomographic image may be acquired while returning to steps suitably. Further alternatively, the following steps may be automatically executed using a computer.

FIG. 7 is a flow chart illustrating a method of acquiring the tomographic image.

(1) In step S1, the measuring beam 106 is caused to enter the subject's eye 107 with the subject's eye 107 fixed on a fixation lamp (not illustrated).

The position of the spherical mirror 160-8 is adjusted with the electrically driven stage 117-2 so that the measuring beam 106 enters the subject's eye 107 with the measuring beam 106 being parallel.

(2) In step S2, an interference fringe is detected with the line sensor 139 while driving the X axis of XY scanner 119 to acquire the tomographic image.

(3) In step S3, the position of the spherical mirror 160-8 is adjusted using the electrically driven stage 117-2 to increase the contrast of the tomographic image while conducting step S2.

(4) In step S4, the aberration of the return beam 108 is measured with the wavefront sensor 155 to calculate the aberration for each optimization wavelength of the spatial light modulators 159-1 and 159-2 (wavelengths of 830 nm and 870 nm). The unit of the aberration is taken as wavelength (respective optimization wavelengths).

(5) In step S5, the acquired aberration is converted into the expression of Zernike polynomials with the personal computer 125 and the data is recorded in the memory of the personal computer 125.

(6) In step S6, such the amount of modulation as to minimize the aberration acquired by the personal computer 125 is calculated for each optimization wavelength of the spatial light modulators 159-1 and 159-2, and the spatial light modulators 159-1 and 159-2 are modulated.

(7) In step S7, feedback control is applied to minimize the aberration using the wavefront sensor 155, the spatial light modulators 159-1 and 159-2, and the personal computer 125, thus controlling the spatial light modulators 159-1 and 159-2 in real time.

(8) In step S8, it is determined whether the aberration is not greater than a setting value. Steps S4 to S7 are repeated until the aberration is converged. The setting value is desirably approximately 0.1 µm (RMS).

(9) In step S9, the interference fringe is detected with the line sensor 139 while driving the X axis of the XY scanner 119 to acquire again the tomographic image.

As described above, according to the present exemplary embodiment, the measuring beam or the return beam is split for each wavelength using the dichroic mirror and aberration is corrected using two spatial light modulators, thereby allowing reducing the influence of dependence of the spatial light modulator on a wavelength and the residue of aberration after the correction of the aberration. As a result, the resolution and the contrast of the tomographic image can be increased.

Furthermore, the aberration of at least either the measuring beam or the return beam is corrected to correct the aberration of a subject itself (the subject's eye), resultantly, enabling increasing the resolution and the contrast of the tomographic image.

The wavefront sensor 155 and the two spatial light modulators are arranged optically conjugate with one another to permit effectively correcting the aberration.

The dichroic mirror or dichroic prism is used to split the measuring beam or the return beam for each wavelength or to combine the measuring beam or the return beam, thus enabling forming an optical path.

The optical path is split and combined by a common dichroic mirror to allow realizing the optical imaging apparatus with a small optical system.

The aberration of the return beam is measured with the wavefront sensor to be calculated for each respective optimization wavelength of the two spatial light modulators.

The calculated aberration is used to allow accurately calculating the amount of modulation of the two spatial light modulators different in optimization wavelength with the personal computer.

The aberration of the return beam is measured for each wavelength using the two wavefront sensors to allow measuring the aberration including the chromatic aberration of the subject's eye, resultantly, enabling acquiring an optical tomographic image high in resolution and contrast.

Light from a light source is split into a measuring beam and a reference beam, and return beam produced from the measuring beam entering the subject is caused to interfere with the reference beam via a reference optical path, thereby allowing capturing the optical tomographic image of the subject by the intensity of an interference signal produced by interference.

This allows providing the optical tomographic image high in resolution and contrast. In the present exemplary embodiment, an interference signal is used in which light from a light source is split into a measuring beam and a reference beam, and a return beam produced from the measuring beam entering the subject is caused to interfere with the reference beam via a reference optical path, thus allowing forming the following method for capturing a tomographic image of the subject.

In a first step, an aberration measuring unit for measuring the aberration of the return beam is used to measure the aberration of the return beam from first and second spatial light modulation units for each different split wavelength.

The first and second spatial light modulation units are optimized for the one and the other of the different split wavelengths, respectively.

In a second step, the aberration of the return beam calculated for each optimization wavelength in the first and second spatial light modulation units is used to calculate the amount of modulation in the first and second spatial light modulation units.

In a third step, at least either the measuring beam or the return beam in the first and second spatial light modulation units is modulated based on the calculated amount of modulation to correct the aberration caused in the subject.

In a second exemplary embodiment of the present invention, an OCT apparatus equipped with an adaptive optical system with a high transverse resolution for capturing the tomographic image (OCT image) of the subject's eye is described below.

In the present exemplary embodiment, similarly with the first exemplary embodiment, a Fourier domain OCT apparatus is formed in which the aberration of the subject's eye is corrected using the spatial light modulator to acquire a tomographic image, allowing providing a good tomographic image irrespective of the diopter and aberration of the subject's eye.

The present exemplary embodiment is characterized in that measuring beam is split into two beams based on wavelength, caused to enter two reflective spatial light modulators, and modulated separately.

In the first exemplary embodiment, the entire optical system is formed of a reflective optical system mainly using spherical mirrors. In the present exemplary embodiment, however, the optical system is formed of a refractive optical system using lenses instead of the spherical mirrors.

Figure 8:
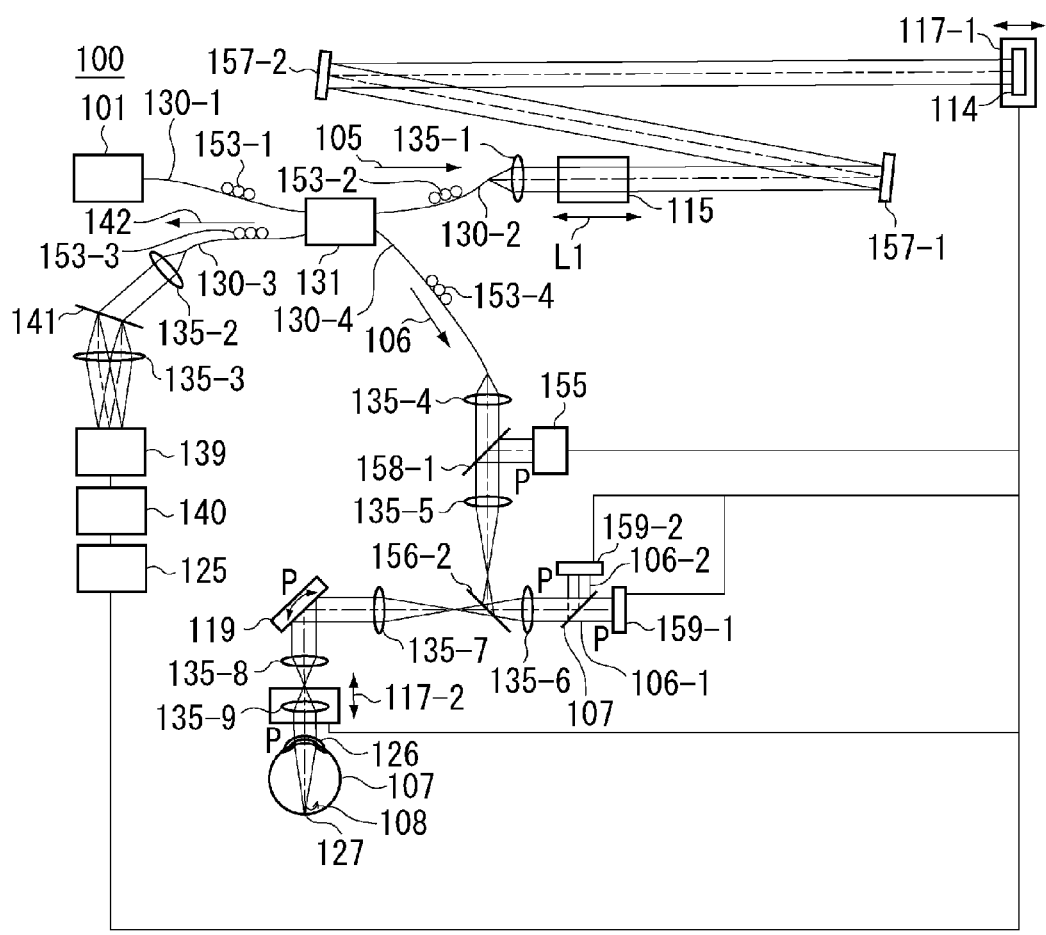
FIG. 8 is a schematic diagram illustrating the general configuration of an OCT apparatus according to a second exemplary embodiment of the present invention.

The general configuration of the OCT apparatus in the present exemplary embodiment is described below with reference to FIG. 8. In the present exemplary embodiment, the components similar to those in FIG. 1 are given the same reference numerals or characters to avoid the description thereof. The measuring beam 106 is led to the subject's eye 107 being an object to be observed via the dichroic mirror 170, the spatial light modulators 159-1 and 159-2, the XY scanner 119, and the lenses 135-4 to 135-9. The measuring beam 106 is split into two beams for each wavelength by the dichroic mirror 170. Then, the two beams are caused to enter the spatial light modulators 159-1 and 159-2 and combined into one beam by the dichroic mirror 170.

The aberration of the return beam 108 is measured with the wavefront sensor 155. There is provided a function that the spatial light modulators 159-1 and 159-2 are controlled to reduce the aberration, thereby a good tomographic image can be acquired irrespective of the diopter and the aberration of the subject's eye 107.

In the present exemplary embodiment, although a reflective spatial light modulator is used, a transmissive spatial light modulator may be used.

Since the light source 101 and the reference optical path are similar to those in the first exemplary embodiment, the description thereof is not repeated.

The optical path of the measuring beam 106 being the characteristic configuration of the present exemplary embodiment is described below.

The measuring beam 106 split by the optical coupler 131 is led to the lens 135-4 via the single mode fiber 130-4 and adjusted so as to be parallel light with a beam diameter of 3 mm.

The measuring beam 106 passes through a first beam splitter 158-1 and is caused to enter a second beam splitter 158-1 via a lens 135-5.

Part of the measuring beam 106 is reflected and is caused to enter the dichroic mirror 170 via the lens 135-6.

The measuring beam 106 is split into a first measuring beam 106-1 and a second measuring beam 106-2.

The dichroic mirror 170 transmits components having a wavelength of approximately 850 nm or more and reflects components having a wavelength shorter than 850 nm.

The first measuring beam 106-1 is modulated by the first spatial light modulator 159-1 and caused to enter again the dichroic mirror 170. The first spatial light modulator 159-1 is optimized for a wavelength of 870 nm.

The second measuring beam 106-2 is modulated by the second spatial light modulator 159-2 and caused to enter again the dichroic mirror 170. The second spatial light modulator 159-2 is optimized for a wavelength of 830 nm.

The spatial light modulators 159-1 and 159-2 are arranged in the direction in which the phase of P polarization (parallel to the paper surface) is modulated.

The first measuring beam 106-1 and the second measuring beam 160-2 are caused to enter the same position of the dichroic mirror 170 and are combined with each other to again turn into one measuring beam 106.

The measuring beam 106 is caused to enter the mirror of the XY scanner 119 via a lens 135-7.

Lenses 135-8 and 135-9 are optical systems for scanning over the retina 127 and has a function to scan the measuring beam 106 over the retina 127 with the vicinity of the cornea 126 set as a fulcrum.

The electrically driven stage 117-2 is movable in the directions indicated by an arrow to allow the position of the attached lens 135-9 to be adjusted and controlled by the personal computer 125.

Adjusting the position of the lens 135-9 focuses the measuring beam 106 on a predetermined layer of the retina 127 of the subject's eye 107 to allow observation.

The above configuration is also adaptable for a case where the subject's eye 107 is abnormal in refraction.

The measuring beam 106 enters the subject's eye 107 to turn into the return beam 108 by reflection and scattering from the retina 127, is led again to the optical coupler 131, and reaches the line sensor 139.

The return beam 108 is split for each wavelength by the dichroic mirror 170, modulated by the spatial light modulators 159-1 and 159-2, and combined again by the dichroic mirror 170.

Part of the return beam 108 split by the beam splitter 158-1 is caused to enter the wavefront sensor 155 to measure the aberration of the return beam 108. The wavefront sensor 155 is electrically connected to the personal computer 125.

The lenses 135-4 to 135-9 are arranged so that the cornea 126, the XY scanner 119, the wavefront sensor 155, and the spatial light modulators 159-1 and 159-2 are made optically conjugate with one another. The positions where they are conjugate with one another are indicated by letter "P."

For this reason, the wavefront sensor 155 can measure the aberration of the subject's eye 107. Furthermore, the spatial light modulators 159-1 and 159-2 can correct the aberration of the subject's eye 107. Still furthermore, the spatial light modulators 159-1 and 159-2 are controlled in real time based on the acquired aberration to allow correcting the aberration caused in the subject's eye 107 and acquiring a tomographic image higher in transverse resolution.

The spherical lens used as the lens 135-9 may be replaced with a cylindrical lens depending on the aberration of the subject's eye 107 (refractive error).

A new lens can be added to the optical path of the measuring beam 106.

Although the reflective liquid crystal spatial phase modulator is used as the spatial light modulators 159-1 and 159-2, the transmissive liquid crystal spatial phase modulator may be used.

The configuration of the measuring system and the method and the procedure for acquiring a tomographic image are similar to those in the first exemplary embodiment, so that the description thereof is not repeated.

Unlike the first exemplary embodiment, in the present exemplary embodiment, the position of the lens 135-9 is adjusted to focus the measuring beam 106 on a predetermined layer of the retina 127 of the subject's eye 107, performing observation.

As described above, according to the present exemplary embodiment, the effect similar to that of the first exemplary embodiment can be achieved. Furthermore, the number of components to be used in the present exemplary embodiment can be made smaller than that in the first exemplary embodiment. It is easier for the present exemplary embodiment to adjust the optical system.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-251422 filed Oct. 30, 2009, which is hereby incorporated by reference herein in its entirety.

What is claimed is:

1. An adaptive optical apparatus comprising:
a wavelength separation unit configured to separate a beam emitted from a light source into a plurality of wavelength band beams;
a plurality of spatial light modulation units configured to modulate the respective plurality of wavelength band beams;
a wavelength combining unit configured to combine the beams modulated by the plurality of spatial light modulation units into a beam; and
an illumination unit configured to illuminate an object with the beam output from the wavelength combining unit.

2. The adaptive optical apparatus according to claim 1, further comprising an aberration measuring unit configured to measure aberration of the object for each of the plurality of wavelength band beams,
wherein the plurality of light modulation units includes:
a first spatial light modulation unit configured to modulate, based on a measuring result provided by the aberration measuring unit, a first beam of the plurality of wavelength band beams at a position optically conjugate to the aberration measuring unit; and
a second spatial light modulation unit located optically parallel with the first spatial light modulation unit and configured to modulate a second beam, different in wavelength band from the first beam, of the plurality of wavelength band beams at a position optically conjugate to the aberration measuring unit.

3. The adaptive optical apparatus according to claim 2, wherein the object includes a subject's eye,
wherein the aberration occurs at an anterior ocular segment of the subject's eye, and
wherein the plurality of spatial light modulation units are located at positions optically conjugate to the anterior ocular segment.

4. The adaptive optical apparatus according to claim 2, wherein a beam used for measuring the aberration by the aberration measuring unit and a beam used for acquiring an image of the object are beams emitted from respective different light sources.

5. The adaptive optical apparatus according to claim 1, wherein the wavelength combining unit is configured to separate, into a plurality of wavelength band beams, a return beam from the object illuminated by the illumination unit,
wherein the plurality of spatial light modulation units is configured to modulate the respective plurality of wavelength band beams, and
wherein the wavelength separation unit is configured to combine the beams modulated by the plurality of spatial light modulation units into a beam.

6. An imaging apparatus comprising:
the adaptive optical apparatus according to claim 1; and
an image acquisition unit configured to acquire an image of the object based on a return beam from the object illuminated by the illumination unit.

7. The imaging apparatus according to claim 6, wherein the adaptive optical apparatus further comprises a separation unit configured to separate the beam from the light source into a beam to be incident on the wavelength separation unit and a reference beam, and
wherein the image acquisition unit is configured to acquire a tomographic image of the object based on interference light caused by interference between the return beam from the object illuminated by the illumination unit and the reference beam.

8. An adaptive optical method comprising:
separating a beam emitted from a light source into a plurality of wavelength band beams; modulating a first beam of the plurality of wavelength band beams by using first spatial light modulation unit;
modulating a second beam of the plurality of wavelength band beams using a second spatial light modulation unit;
combining the beams modulated by the first and second spatial light modulation units into a beam; and
illuminating an object with the combined beam.

9. The adaptive optical apparatus according to claim 1, wherein the plurality of spatial light modulation units includes:
a first spatial light modulation unit configured to modulate a first beam of the plurality of wavelength band beams; and
a second spatial light modulation unit located in optically parallel with the first light modulation unit and configured to modulate a second beam, different in wavelength band from the first beam, of the plurality of wavelength band beams.

10. The adaptive optical apparatus according to claim 1, further comprising an aberration measuring unit configured to measure aberration of the object for each of the plurality of wavelength band beams,
wherein the plurality of spatial light modulation units includes:
a first spatial light modulation unit configured to modulate, based on a measuring result provided by the aberration measuring unit, a first beam of the plurality of wavelength band beams; and
a second spatial light modulation unit located optically parallel with the first spatial light modulation unit and configured to modulate a second beam based on a measuring result provided by the aberration measuring unit, wherein the second beam is different in wavelength band from the first beam, of the plurality of wavelength band beams.

11. The adaptive optical apparatus according to claim 1, further comprising:
an aberration measuring unit configured to measure aberration of the object for each of the plurality of wavelength band beams; and
a calculation unit configured to calculate aberration for each predetermined wavelength of the plurality of spatial light modulation units based on a measuring result provided by the aberration measuring unit,
wherein the plurality of spatial light modulation units modulate the plurality of wavelength band beams based on a calculation result provided by the calculation unit.

12. The adaptive optical apparatus according to claim 1, wherein the illumination unit includes:
a reflective member configured to illuminate the object with the beam combined by the wavelength combining unit; and
an adjusting unit configured to adjust a position of the reflective member so as to focus on a predetermined position of the object.

13. The adaptive optical apparatus according to claim 1, wherein the plurality of spatial light modulation units are a plurality of reflective liquid-crystal spatial phase modulators.

14. An adaptive optical apparatus comprising:
a wavelength separation unit configured to separate a beam emitted from a light source into a plurality of wavelength band beams;
a first light modulation unit configured to modulate a first beam of the plurality of wavelength band beams;
a second light modulation unit located optically parallel with the first light modulation unit and configured to modulate a second beam, different in wavelength band from the first beam, of the plurality of wavelength band beams;
a wavelength combining unit configured to combine the beams modulated by the first and second light modulation units into a beam; and
an illumination unit configured to illuminate an object with the beam output from the wavelength combining unit.

15. An adaptive optical apparatus comprising: a wavelength separation unit configured to separate a beam emitted from a light source into a plurality of wavelength band beams; a first light modulation unit configured to modulate a first beam of the plurality of wavelength band beams; and a second light modulation unit configured to modulate a second beam, different in wavelength band from the first beam, of the plurality of wavelength band beams;
a wavelength combining unit configured to combine the beams modulated by the plurality of spatial light modulation units into a beam;
and an illumination unit configured to illuminate an object with the beam output from the wavelength combining unit.

16. An optical image capturing apparatus in which light from a light source is taken as measuring light and an image of a subject is captured with an intensity of return light caused by the measuring light with which the subject is irradiated, the optical image capturing apparatus comprising:
a splitting unit configured to split an optical path into first and second optical paths based on wavelength in the optical path from the light source to the subject;
a first spatial light modulation unit configured to correct aberration of at least one of the measuring light and the return light on the first optical path;
a second spatial light modulation unit configured to correct aberration of at least one of the measuring light and the return light on the second optical path; and
a combining unit configured to combine the first optical path and the second optical path.

17. The adaptive optical apparatus according to claim 15, further comprising:
an aberration measuring unit configured to measure aberration of the object for each of the plurality of wavelength band beams; and
a calculation unit configured to calculate aberration for each predetermined wavelength of the plurality of spatial light modulation units based on a measuring result provided by the aberration measuring unit,
wherein the plurality of spatial light modulation units modulate the plurality of wavelength band beams based on a calculation result provided by the calculation unit.

18. The adaptive optical method according to claim 8, further comprising:
measuring an aberration of the object for each of the plurality of wavelength band beams; and
calculating an aberration for each predetermined wavelength of the plurality of spatial light modulation units based on a measuring result provided by the measured aberration,
wherein the plurality of spatial light modulation units modulate the plurality of wavelength band beams based on the calculated aberration.

* * * * *